United States Patent
Bon et al.

(10) Patent No.: US 8,686,180 B2
(45) Date of Patent: Apr. 1, 2014

(54) PROCESS FOR PREPARING AMINOBENZOFURAN DERIVATIVES

(71) Applicant: SANOFI, Paris (FR)

(72) Inventors: Xavier Bon, Paris (FR); Corinne Leroy, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/628,867

(22) Filed: Sep. 27, 2012

(65) Prior Publication Data

US 2013/0023677 A1 Jan. 24, 2013

Related U.S. Application Data

(63) Continuation of application No. PCT/FR2011/050726, filed on Mar. 31, 2011.

(30) Foreign Application Priority Data

Apr. 1, 2010 (FR) ...................... 10 52481

(51) Int. Cl.
*C07C 229/00* (2006.01)

(52) U.S. Cl.
USPC .......................................................... 560/45

(58) Field of Classification Search
USPC .......................................................... 560/45
See application file for complete search history.

(56) References Cited

U.S. PATENT DOCUMENTS

| | | | |
|---|---|---|---|
| 4,666,931 A | 5/1987 | Ohishi et al. | |
| 5,223,510 A | 6/1993 | Gubin et al. | |
| 6,828,448 B2 | 12/2004 | Fino et al. | |
| 6,846,936 B2 | 1/2005 | Biard | |
| 2012/0065411 A1 | 3/2012 | Kretzschmar et al. | |
| 2012/0077995 A1 | 3/2012 | Kretzschmar et al. | |
| 2012/0289717 A1 | 11/2012 | Friesz et al. | |
| 2012/0330036 A1 | 12/2012 | Friesz et al. | |
| 2013/0012729 A1 | 1/2013 | Bailly et al. | |
| 2013/0023678 A1 | 1/2013 | Priem et al. | |

FOREIGN PATENT DOCUMENTS

| | | | | |
|---|---|---|---|---|
| EP | 0471609 | * | 8/1991 | ........... C07D 307/81 |
| EP | 0471609 A1 | | 2/1992 | |
| WO | WO 03/040120 A1 | | 5/2003 | |
| WO | WO 2012/127173 | | 9/2012 | |
| WO | WO 2012/131408 | | 10/2012 | |
| WO | WO 2012/131409 | | 10/2012 | |
| WO | WO 2012/131410 | | 10/2012 | |
| WO | WO 2013/014478 | | 1/2013 | |
| WO | WO 2013/014479 | | 1/2013 | |
| WO | WO 2013/014480 | | 1/2013 | |

OTHER PUBLICATIONS

Tanaka et al. Bulletin of the Chemical Society of Japan vol. 40 Issue: 7 pp. 1724-1726, 1967.*
U.S. Appl. No. 13/742,810, filed Jan. 16, 2013, Bailly, et al.
U.S. Appl. No. 13/742,816, filed Jan. 16, 2013, Bon, et al.
U.S. Appl. No. 13/711,891, filed Dec. 12, 2012, Friesz.
U.S. Appl. No. 13/740,505, filed Jan. 14, 2013, Friesz, et al.
U.S. Appl. No. 13/638,484, filed Aug. 30, 2012, Bailly, et al.
International Search Report for WO2011/121245 dated Oct. 6, 2011.
Abramenko, et al., Polymethine Dyes—Furo[2,3-g] Benzothiazole Derivatives, Chemistry of Heterocyclic Compounds, (A Translation of Khimiya Geterotsiklicheskikh Soedinenii) vol. 11, (1975), pp. 1361-1364.
Bourgery, et al., Synthesis and Antiarrhythmic Activity of New Benzofuran Derivatives, Journal of Medicinal Chemistry, (1981), vol. 24, No. 2, pp. 159-167.
Roshchin, et al., Synthesis of Benzofurans via Pd2+-Catalyzed Oxidative Cyclization of 2-Allylphenols, Journal of Organornettallic Chemistry, vol. 560, No. 1-2, (1998), pp. 163-167.
Tanaka, Studies on 5-Aminosalicylaldehyde Derivatives. II. Reduction of 5-(p-Sulfophenylazo) Salicylaldehyde Through Poly(5-Nitrilosalicylidene) to 5-Aminosalicylaldehyde Derivatives, Bulletin of the Chemical Society of Japan, vol. 40, No. 7, (1967), pp. 1724-1726.

* cited by examiner

*Primary Examiner* — Nizal Chandrakumar
(74) *Attorney, Agent, or Firm* — Scully, Scott, Murphy & Presser, P.C.

(57) ABSTRACT

This disclosure relates to a process for preparing 5-aminobenzofuran derivatives of general formula (I):

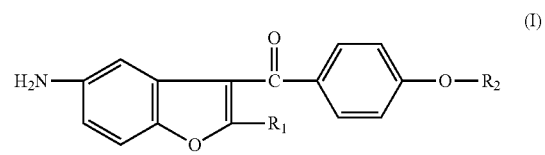

in which $R_1$ and $R_2$ are as defined in the description,
by treating a 5-N-alkylamidobenzofuran derivative of general formula (II):

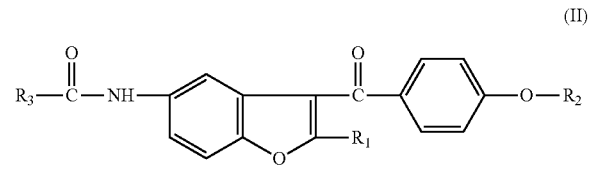

in which $R_1$, $R_2$, and $R_3$ are as defined in the description, with a strong acid, so as to form an acid addition salt of the compound of formula (I), which salt is itself treated, if necessary, with a basic agent so as to form this compound of formula (I) in free base form.

3 Claims, No Drawings

PROCESS FOR PREPARING AMINOBENZOFURAN DERIVATIVES

The present invention relates generally to the preparation of aminobenzofuran derivatives.

More specifically, the invention relates to a process for preparing 5-aminobenzofuran derivatives of general formula:

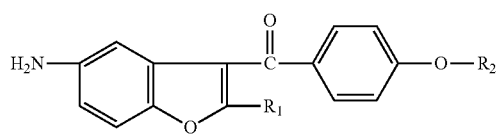

and also to the addition salts thereof, in which $R_1$ represents hydrogen or an alkyl group and $R_2$ represents an alkyl or dialkylaminoalkyl group.

In formula I above:
- $R_1$ represents, in particular, a linear or branched $C_1$-$C_8$ alkyl group, especially a linear or branched $C_1$-$C_4$ alkyl group such as methyl, ethyl, n-propyl, isopropyl, n-butyl, sec-butyl or tert-butyl,
- $R_2$ represents, in particular, a linear or branched $C_1$-$C_8$ alkyl group, especially a linear or branched $C_1$-$C_4$ alkyl group such as methyl, ethyl, n-propyl, isopropyl, n-butyl, sec-butyl or tert-butyl or alternatively a dialkylaminoalkyl group in which each linear or branched alkyl group is of $C_1$-$C_8$ and especially in which each linear or branched alkyl group is of $C_1$-$C_4$, such as methyl, ethyl, n-propyl, isopropyl, n-butyl, sec-butyl or tert-butyl.

In particular, $R_1$ represents n-butyl and $R_2$ represents 3-(di-n-butylamino)propyl.

Among the compounds of formula I above, 2-n-butyl{4-[3-(di-n-butylamino)propoxy]benzoyl}-5-aminobenzofuran described in patent EP 0 471 609 proves to be particularly useful as an intermediate product for the final preparation of aminoalkoxybenzoylbenzofuran derivatives, in particular for the preparation of 2-n-butyl-3-{4-[3-(di-n-butylamino)propoxy]benzoyl}-5-methanesulfonamidobenzofuran, commonly known as dronedarone, and also the pharmaceutically acceptable salts thereof. This methanesulfonamidobenzofuran derivative was described in the patent mentioned previously, along with its therapeutic applications, especially in the cardiovascular field where it proved to be particularly advantageous, for example as an antiarrhythmic agent.

In addition, that same patent EP 0 471 609 disclosed a process for synthesizing 2-n-butyl-3-{4-[3-(di-n-butylamino)propoxy]benzoyl}-5-aminobenzofuran using 2-n-butyl-3-{4-[3-(di-n-butylamino)propoxy]benzoyl}-5-nitrobenzofuran, which is reduced, under pressure, with hydrogen in the presence of platinum oxide as catalyst, to give the desired compound.

However, this process is not without drawbacks inherent especially to the type of reaction used, namely hydrogenation under pressure, which entails an industrial risk.

The search for a process for preparing 2-n-butyl-3-{4-[3-(di-n-butylamino)propoxy]benzoyl}-5-aminobenzofuran that is capable of overcoming this drawback and disadvantage thus remains of fundamental interest.

U.S. Pat. No. 4,666,931 and the articles Chemistry of Heterocyclic Compounds (1975), vol. 11, pp. 1361-1364, Journal of Organometallic Chemistry (1998), vol. 560, pp. 163-167 and Bulletin of the Chemical Society of Japan (1967), vol. 40, pp. 1724-1726 describe N-phenylalkylamide and 5-N-alkylamidobenzofuran derivatives, but do not in any way suggest their use in the preparation of compounds of formula (I) according to the invention.

Furthermore, WO 03/040 120 describes a process for preparing dronedarone, in six steps, using a Friedel-Crafts reaction. However, that document does not describe the preparation of dronedarone comprising a simple step of treating a 5-N-alkylamidobenzofuran derivative of formula (IIa) according to the invention with a strong acid.

According to the invention, the 5-aminobenzofuran derivatives of formula I may be prepared by treating, with a strong acid such as a hydracid, for example hydrofluoric acid, a 5-N-alkylamidobenzofuran derivative of general formula:

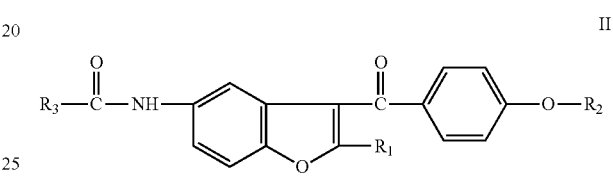

in which $R_1$ and $R_2$ have the same meaning as previously and $R_3$ represents a linear or branched $C_1$-$C_4$ alkyl group, for example methyl, to form an acid-addition salt of the compound of formula I, which salt is itself treated, if necessary, with a basic agent such as an alkali metal hydroxide, to give this compound of formula I in free base form.

Hereinabove and hereinbelow, unless specifically mentioned:

The term "strong acid" means any chemical compound which has a very high capacity for introducing protons into the reaction medium and which is characterized, in aqueous solution, by a pKa of less than or equal to 1. The term "strong acid" especially means any hydracid such as chosen from hydrochloric acid, hydrobromic acid and hydrofluoric acid.

The term "basic agent" means any chemical compound which has a high affinity for protons $H^+$ and which is characterized, in aqueous solution, by a pKa of greater than 7. The term "basic agent" especially means bases of any type such as chosen from organic bases, weak bases and strong bases, chosen especially from tertiary amines, alkali metal carbonates and alkali metal hydroxides.

The term "strong base" means any chemical compound which has a very high affinity for protons $H^+$ and which is characterized, in aqueous solution, by a pKa of greater than 14. The term "strong base" especially means any alkali metal hydroxide, such as chosen from sodium hydroxide and potassium hydroxide.

The acid treatment may be undertaken in a polar solvent such as an alcohol, for example ethanol, using an acid generally in excess, for example from 1 to 6 equivalents of this acid per equivalent of compound of formula II.

Moreover, the acid-addition salt of the compound of formula I may be treated with a basic agent, after isolation from the reaction medium in which it is formed or, on the contrary, in situ, i.e. within this same reaction medium.

The starting compounds of formula II may be prepared according to the following reaction scheme:

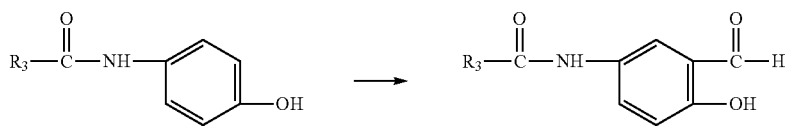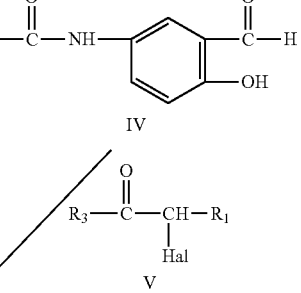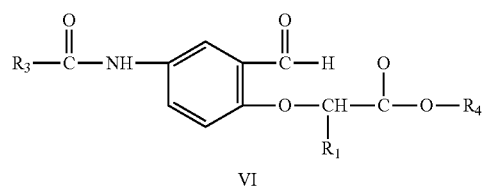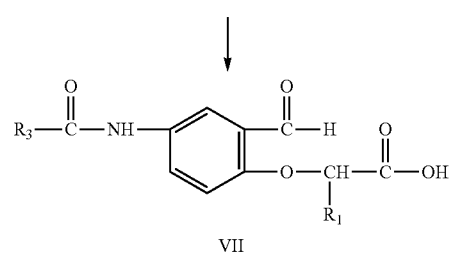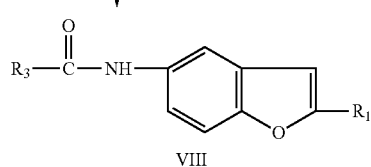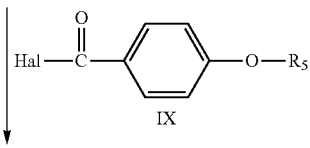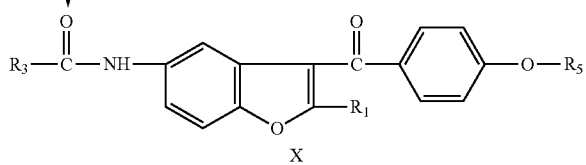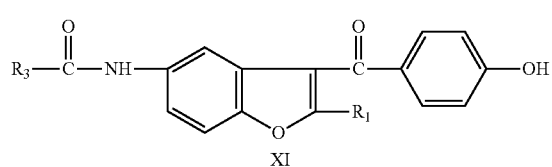

-continued

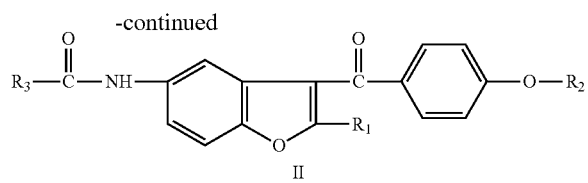

II i.e. starting with a compound of formula III, in which $R_3$ has the same meaning as previously, which compound is heated in the presence of trifluoroacetic acid in a suitable solvent, usually an amine, for example hexamethylenetetramine, to form an N-phenylalkylamide derivative of formula IV in which $R_3$ has the same meaning as previously.

This amide of formula IV is then reacted with an ester of formula V in which $R_1$ has the same meaning as previously, $R_4$ represents a linear or branched $C_1$-$C_4$ alkyl group and Hal represents a halogen, for example bromine, in the presence of a basic agent, generally a weak base such as an alkali metal carbonate, and by heating in a polar solvent so as to form an ester of formula VI in which $R_1$, $R_3$ and $R_4$ have the same meaning as previously.

The ester of formula VI is then saponified in the presence of a strong base, generally an alkali metal hydroxide, the reaction usually taking place at room temperature and in a suitable solvent, for example an ether, to give a salt of a carboxylic acid derivative, which is treated with a strong acid, such as a hydracid, for example hydrofluoric acid, which gives a carboxylic acid derivative of formula VII in which $R_1$ and $R_3$ have the same meaning as previously.

The compound of formula VII thus produced is then cyclized to a benzofuran derivative of formula VIII in which $R_1$ and $R_3$ have the same meaning as previously, this being done in the presence of an organic base, generally a tertiary amine, and of a benzenesulfonyl chloride. The reaction is usually performed by heating in a suitable solvent, in general an aprotic solvent such as an aromatic hydrocarbon or an ether.

The benzofuran derivative of formula VIII thus obtained is then coupled with an acyl halogen of formula IX in which $R_5$ represents a linear or branched $C_1$-$C_4$ alkyl group, for example methyl, and Hal has the same meaning as previously, for example chlorine, this being done in the presence of a Lewis acid, for example ferric chloride, and in a non-polar solvent, for example a halogenated compound. The reaction medium thus obtained is then hydrolyzed in the presence of a strong acid, for example a hydracid, to produce a ketone of formula X in which $R_1$, $R_3$ and $R_5$ have the same meaning as previously.

This ketone of formula X is then dealkylated by heating in the presence of aluminum chloride and in a non-polar solvent, usually a halogenated solvent such as chlorobenzene, to form a 4-hydroxyphenyl derivative of formula XI in which $R_1$ and $R_3$ have the same meaning as previously. Thereafter, the compound of formula XI is reacted with an alkyl halide of formula XII in which $R_2$ has the same meaning as previously and Hal has the same meaning as previously, for example chlorine, the reaction taking place in the presence of a basic agent such as an alkali metal carbonate and by heating usually in a polar solvent such as a ketone, to give the desired compound of formula II.

Another subject of the present invention relates to the N-phenylalkylamide derivatives of general formula:

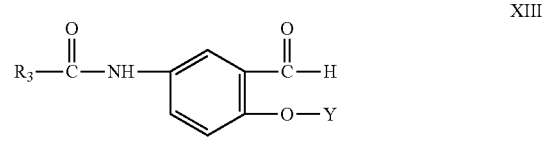

in which $R_3$ has the same meaning as previously and Y represents hydrogen or a group of general formula:

in which $R_1'$ and $R_6$ represent, independently of each other, hydrogen or a linear or branched $C_1$-$C_4$ alkyl group, to the exclusion of the compounds for which $R_3$=Me, Et or isopropyl and Y=H.

Among the N-phenylalkylamide derivatives of general formula XIII, mention may be made of those in which $R_3$ represents a linear or branched $C_1$-$C_4$ alkyl group and Y represents a group of general formula XIV:

in which $R_1'$ and $R_6$ represent, independently of each other, hydrogen or a linear or branched $C_1$-$C_4$ alkyl group.

Among the compounds of formula XIII, mention may be made of the following subgroup in which Y represents hydrogen or the group XIV in which $R_1$ represents n-butyl, and also of the compounds of formula XIII in which $R_3$ represents methyl.

Moreover, among the compounds of formula XIII, mention may further be made of the subgroups in which $R_3$ represents methyl, Y represents hydrogen or the group XIV in which $R_1$ represents n-butyl and $R_6$ represents hydrogen or methyl.

Consequently, the subgroups of the N-phenylalkylamide derivatives of formula XIII may be those in which:

a) $R_3$ represents methyl and Y represents the group XIV in which $R_1'$ represents n-butyl and $R_6$ represents methyl, b) $R_3$ represents methyl and Y represents the group XIV in which $R_1'$ represents n-butyl and $R_6$ represents hydrogen.

In addition, another subject of the present invention concerns the 5-N-alkylamidobenzofuran derivatives of general formula:

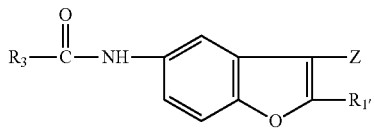

in which $R_1'$ and $R_3$ have the same meaning as previously and Z represents hydrogen or a group of general formula:

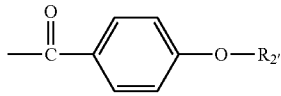

in which $R_2'$ represents hydrogen, a linear or branched $C_1$-$C_4$ alkyl group or a dialkylaminoalkyl group in which each linear or branched alkyl group is of $C_1$-$C_4$,
to the exclusion of the compounds for which $R_3$=Me, Z=H and $R'_1$=H, Me, Et or n-Bu.

Among the 5-N-alkylamidobenzofuran derivatives of general formula XV, mention may be made of those in which $R_1'$ represents hydrogen or a linear or branched $C_1$-$C_4$ alkyl group, $R_3$ represents a linear or branched $C_1$-$C_4$ alkyl group and Z represents a group of general formula XVI:

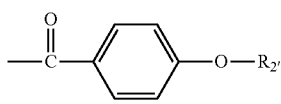

in which $R_2'$ represents hydrogen, a linear or branched $C_1$-$C_4$ alkyl group or a dialkylaminoalkyl group in which each linear or branched alkyl group is of $C_1$-$C_4$.

Among the compounds of formula XV above, mention may be made of those in which $R_1'$ represents n-butyl, and also of the compounds of formula XV in which $R_3$ represents methyl.

Moreover, among the compounds of formula XV, mention may be made of the following subgroups in which Z represents hydrogen or a group XVI in which $R_2'$ represents hydrogen, methyl or 3-(di-n-butylamino)propyl.

Moreover, among the compounds of formula XV, mention may also be made of those in which $R_1'$ represents n-butyl, $R_3$ represents methyl and $R_2'$ represents hydrogen, methyl or 3-(di-n-butylamino)propyl.

Consequently, subgroups of the 5-N-alkylamidobenzofuran derivatives of formula XV may be those in which:
a) $R_1'$ represents n-butyl, $R_3$ represents methyl and Z represents the group XVI in which $R_2'$ represents hydrogen,
b) $R_1'$ represents n-butyl, $R_3$ represents methyl and Z represents the group XVI in which $R_2'$ represents methyl,
c) $R_1'$ represents n-butyl, $R_3$ represents methyl and Z represents the group XVI in which $R_2'$ represents 3-(di-n-butylamino)propyl.

An additional subject of the present invention concerns the use of compounds of formula II for the preparation of dronedarone and of pharmaceutically acceptable salts thereof.

Thus, according to another characteristic of the present invention, dronedarone of formula:

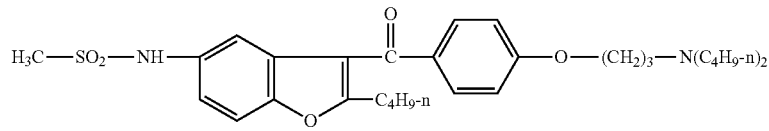

and pharmaceutically acceptable salts thereof, may be obtained:

a) by treating a 5-N-alkylamidobenzofuran derivative of general formula:

II$_a$

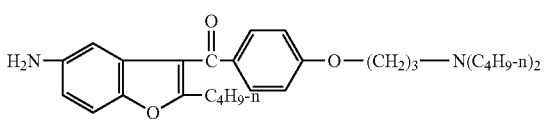

in which $R_3$ has the same meaning as previously, for example methyl, with a strong acid such as a hydracid, for example hydrofluoric acid, to form an addition salt (also known as an "acid-addition salt") of 2-n-butyl-3-{4-[3-(di-n-butylamino)propoxy]benzoyl}-5-aminobenzofuran of formula:

I$_a$ which salt is itself treated with a basic agent such as an alkali metal hydroxide, to give this compound of formula I$_a$ in free base form, b) by coupling this 5-aminobenzofuran derivative of formula I$_a$ with methanesulfonyl chloride to form the dronedarone compound in free base form, which may be reacted, if necessary, with an acid to produce a pharmaceutically acceptable salt of this compound.

The 5-N-alkylamidobenzofuran derivatives of formula II$_a$ may themselves be obtained by performing a sequence of steps according to which:

a) an N-phenylalkylamide derivative of general formula:

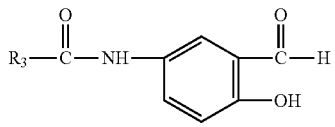

IV in which $R_3$ has the same meaning as previously, is reacted with an ester of general formula:

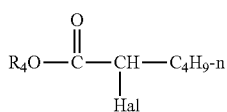

Va in which $R_4$ and Hal have the same meaning as previously, and in doing so in the presence of a basic agent and by heating in a polar solvent to form an ester of general formula:

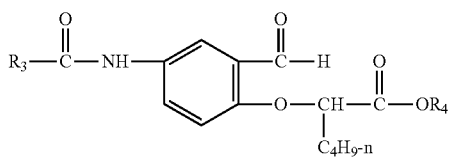

VIa in which $R_3$ and $R_4$ have the same meaning as previously,
b) the ester of formula $VI_a$ is saponified in the presence of a strong base, the reaction proceeding at room temperature and in a suitable solvent, to give a carboxylic acid derivative, which is treated with a strong acid to form the carboxylic acid derivative of general formula:

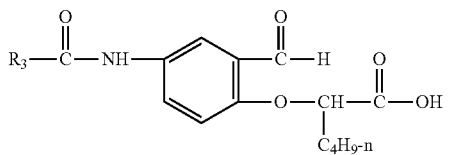

VIIa in which $R_3$ has the same meaning as previously,
c) the carboxylic acid derivative of formula $VII_a$ is cyclized by heating in an aprotic solvent and in the presence of an organic base and a benzenesulfonyl halide to form a benzofuran derivative of general formula:

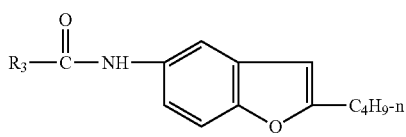

VIIIa in which $R_3$ has the same meaning as previously,
d) the benzofuran derivative of formula $VIII_a$ is coupled with an acyl halide of general formula:

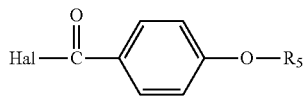

IX in which $R_5$ and Hal have the same meaning as previously, this being done in the presence of a Lewis acid and in a non-polar solvent, the reaction medium thus formed then being hydrolyzed in the presence of a strong acid to form a ketone of general formula:

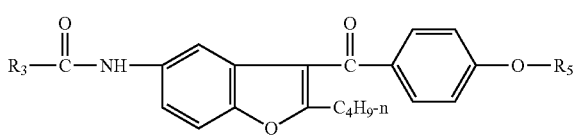

Xa in which $R_3$ and $R_5$ have the same meaning as previously,
e) the ketone of formula $X_a$ is dealkylated in the presence of aluminum chloride and in a non-polar solvent to form a 4-hydroxyphenyl derivative of general formula:

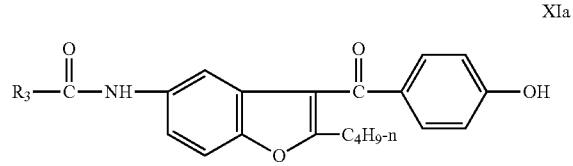

XIa in which $R_3$ has the same meaning as previously,
f) the 4-hydroxyphenyl derivative of formula XI, is reacted with an alkyl halide of general formula:

Hal-$(CH_2)_3$—$N(C_4H_9$-$n)_2$     XIIa in which Hal has the same meaning as previously, the reaction taking place in the presence of a basic agent and by heating in a polar solvent, to form the desired compound of formula $II_a$.

The non-limiting example that follows illustrates the invention.

Preparations

A. N-(3-Formyl-4-hydroxyphenyl)acetamide
(Compound IV: $R_3$=$CH_3$)

25 g of N-(4-hydroxyphenyl)acetamide (0.165 mol; 1 equivalent) and 92.7 g of trifluoroacetic acid (0.661 mol; 4 equivalents) are placed in a 500 ml reactor. The mixture is stirred, and 92.7 g of hexamethylenetetramine (0.661 mol; 4 equivalents) are then added portionwise. The reaction is exothermic. A temperature of 70° C. is maintained over 18 hours, while monitoring the reaction progress by thin-layer chromatography (eluent: 8/2 toluene/methanol). The reaction medium is allowed to warm to room temperature. It becomes thick, and is diluted by addition of 200 ml of water to facilitate the stirring. 100 ml of ethyl acetate are then added. Stirring is continued and the phases are allowed to separate by settling. 300 ml of water and 200 ml of ethyl acetate are added, the mixture is stirred and the phases are then allowed to separate by settling. The aqueous phase is removed first, then the organic phase. The organic phase is then washed twice with 150 ml of water in total to collect, after phase separation, a new organic phase and a new aqueous phase. This new organic phase is then concentrated on a rotary evaporator (T=45° C.; 50 mmHg). 14 g of the desired compound are thus obtained in the form of crystals recovered from an orange-red solution.

$^1$H NMR (DMSO-$d_6$)

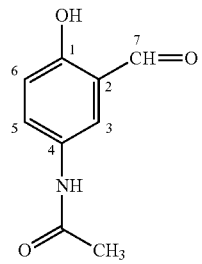

| Chemical shifts<br>δ ± 0.01 ppm | Multiplicity | Integration | Coupling constants<br>(\|J\| ± 0.5 Hz) | Assignment |
|---|---|---|---|---|
| 2.00 | Singlet | 3 | — | CH$_3$ |
| 6.94 | Doublet | 1 | $^3J_{H6-H5}$ = 9.0 Hz | H (6) |
| 7.64 | Doubled doublet | 1 | $^3J_{H5-H5}$ = 9.0 Hz<br>$^4J_{H5-H3}$ = 2.5 Hz | H (5) |
| 7.88 | Doublet | 1 | $^4J_{H3-H5}$ = 2.5 Hz | H (3) |
| 9.86 | Broad singlet | 1 | — | NH |
| 10.24 | Singlet | 1 | — | CH (7) |
| 10.44 | Broad singlet | 1 | — | OH |

$^{13}$C NMR (DMSO-$d_6$)

| Chemical shifts<br>δ ± 0.1 ppm | Number of carbons | Assignment |
|---|---|---|
| 23.6 | 1 | CH$_3$ |
| 117.3 | 1 | CH(6) |
| 118.5 | 1 | CH(3) |
| 121.8 | 1 | Quaternary C (2) |
| 127.9 | 1 | CH(5) |
| 131.5 | 1 | Quaternary C (4) |
| 156.6 | 1 | Quaternary C (1) |
| 167.9 | 1 | CH—$\underline{C}$=O |
| 191.0 | 1 | CH(7)-aldehyde- |

B. Methyl 2-(2-formyl-4-N-acetamidophenoxy)hexanoate (Compound VI: R$_1$=n-C$_4$H$_9$; R$_3$=CH$_3$; R$_4$=CH$_3$)

5.1 g of N-(3-formyl-4-hydroxyphenyl)acetamide (compound IV) (0.028 mmol; 1 equivalent) and 10 ml of N,N-dimethylformamide (2 volumes) are placed in a conical flask. The reaction mixture is stirred at 50° C., which gives a first dark orange solution.

Potassium carbonate (0.6 equivalent) and 8 ml of N,N-dimethylformamide (1.5 volumes) are placed in a 50 ml reactor. The mixture is stirred at 50° C. and the first solution is then added. Stirring is continued at 50° C. for 1 hour, which gives a second solution.

6.5 g of methyl 2-bromoheptanoate (compound V) (1.05 equivalents) are then prepared in 5 ml of N,N-dimethylformamide, and are added to the second solution, and the whole is then stirred at 75° C. for 5 hours. The reaction mixture is taken up in 15 ml of dichloromethane and 15 ml of water, stirred, and the two phases are separated by settling. The dichloromethane phase is washed with water (3×10 ml) and this phase is then concentrated on a rotary evaporator to give 9 g of brown crystals. These crystals are reslurried in 20 ml of water and then crushed by spatula to recover finely divided crystals suspended in the water. The mixture is then filtered, which gives 8.9 g of wet crystals, which are taken up in 25 ml of methyl tert-butyl ether. 5 ml of methanol are added and the mixture is then refluxed for 1 hour in the presence of carbon black (0.1 g). The hot reaction mixture is filtered through Celite and then concentrated to 50%. 4 g of a precipitate with an organic purity of 98% are thus recovered. The filtrate is again concentrated and then stirred at room temperature, which brings about the appearance of a new precipitate, which is filtered off and dried. 1.6 g of the desired compound are thus recovered.

$^1$H NMR (CDCl$_3$)

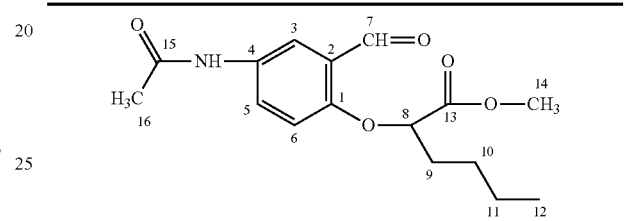

| Chemical shifts<br>δ ± 0.01 ppm | Multiplicity | Integration | Coupling constants<br>(\|J\| ± 0.5 Hz) | Assignment |
|---|---|---|---|---|
| 0.92 | Triplet | 3 | $^3J_{CH3-CH2}$ = 7.5 Hz | CH$_3$ (12) |
| 1.38 | Sextet | 2 | $^3J_{CH2-CH3}$ = 7.5 Hz<br>$^3J_{CH2-CH2}$ = 7.5 Hz | CH$_2$ (11) |
| 1.49 | Quintet | 2 | $^3J_{CH2-CH2}$ = 7.5 Hz | CH$_2$ (10) |
| 2.01 | Multiplet | 2 | — | CH$_2$ (9) |
| 2.15 | Singlet | 3 | — | CH$_3$ (16) |
| 3.74 | Singlet | 3 | — | CH$_3$ (14) |
| 4.74 | Triplet | 2 | $^3J_{CH-CH2}$ = 6.0 Hz | CH (8) |
| 6.79 | Doublet | 1 | $^3J_{H6-H5}$ = 9.0 Hz | H (6) |
| 7.62 | Doublet | 1 | $^4J_{H3-H5}$ = 3.0 Hz | H (3) |
| 8.09 | Doubled doublet | 1 | $^3J_{H5-H6}$ = 9.0 Hz<br>$^4J_{H5-H3}$ = 3.0 Hz | H (5) |
| 8.11 | Broad singlet | 1 | — | NH |
| 10.51 | Singlet | 1 | — | CH (7) |

$^{13}$C NMR (CDCl$_3$)

| Chemical shifts<br>δ ± 0.1 ppm | Number of carbons | Assignment |
|---|---|---|
| 13.9 | 1 | CH$_3$ (12) |
| 22.3 | 1 | CH$_2$ (11) |
| 24.3 | 1 | CH$_3$ (16) |
| 27.3 | 1 | CH$_2$ (10) |
| 32.4 | 1 | CH$_2$ (9) |
| 52.5 | 1 | CH$_3$ (14) |
| 77.4 | 1 | CH(7) |
| 114.1-119.2-128.4 | 3 | CH(3, 5, 6) |
| 125.4 | 1 | Quaternary C (2) |
| 132.7 | 1 | Quaternary C (4) |
| 156.8 | 1 | Quaternary C (1) |
| 168.9-171.6 | 2 | C=O (13, 15) |
| 189.5 | 1 | CH(7)-aldehyde- |

C. 2-(2-Formyl-4-N-acetamidophenoxy)hexanoic acid (Compound VII: R$_1$=n-C$_4$H$_9$; R$_3$=CH$_3$)

3.5 g of methyl 2-(2-formyl-4-N-acetamidophenoxy)hexanoate (compound VI) (0.0114 mol; 1 equivalent) and then about 15 ml of methyl tert-butyl ether (about 3 volumes) are placed in a round-bottomed flask. The mixture is stirred at room temperature so as to form a suspension of this ester. A sodium hydroxide solution (0.57 g/5 ml of water) is then added and the mixture is stirred for 1 hour. 5 ml of water are then added and stirring is continued until total dissolution of the ester compound is obtained. Two phases are thus recovered, one of methyl tert-butyl ether, the other an aqueous phase containing a carboxylic acid. These two phases are separated by settling and 5 ml of 36% hydrochloric acid/5 ml of water are then added to the aqueous phase (pH=14). The aqueous phase is brought to pH 1, which brings about the appearance of a yellow precipitate, and is then stirred for 30 minutes at room temperature. The precipitate is filtered off through a sinter, which gives 3.1 g of an orange-yellow mass with an organic purity of 99.7%. This mass is taken up in 20 ml of acetone, brought to reflux and then filtered while hot. 1.7 g of wet white compound are thus obtained, and are dried to give 1.5 g of the desired compound in the form of white crystals with an organic purity of 99.7%.

$^1$H NMR (DMSO-d$_6$)

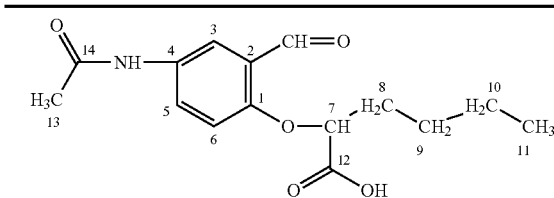

| Chemical shifts δ ± 0.01 ppm | Multiplicity | Integration | Coupling constants (|J| ± 0.5 Hz) | Assignment |
|---|---|---|---|---|
| 0.89 | Triplet | 3 | $^3J_{CH3-CH2}$ = 7.0 | CH$_3$ (11) |
| 1.35 | Sextet | 2 | $^3J_{CH2-CH3}$ = 7.0<br>$^3J_{CH2-CH2}$ = 7.0 | CH$_2$ (10) |
| 1.48 | Quintet | 2 | $^3J_{CH2-CH2}$ = 7.0 | CH$_2$ (9) |
| 1.94 | Broad doublet of triplets | 2 | $^3J_{CH2-CH2}$ = 7.0<br>$^3J_{CH2-CH}$ = 6.0 | CH$_2$ (8) |
| 2.02 | Singlet | 3 | — | CH$_3$ (13) |
| 4.90 | Triplet | 1 | $^3J_{H7-H8}$ = 6.0 | CH (7) |
| 7.07 | Doublet | 1 | $^3J_{H6-H5}$ = 9.0 | CH (6) |
| 7.76 | Doubled doublet | 1 | $^3J_{H5-H6}$ = 9.0<br>$^4J_{H5-H3}$ = 2.5 | CH (5) |
| 7.93 | Doublet | 1 | $^4J_{H3-H5}$ = 2.5 | CH (3) |
| 9.98 | Singlet | 1 | — | NH |
| 10.43 | Singlet | 1 | — | CH (aldehyde) |
| 13.12 | Broad singlet | 1 | — | COOH |

$^{13}$C NMR (DMSO-d$_6$)

| Chemical shifts δ ± 0.1 ppm | Number of carbons | Assignment |
|---|---|---|
| 13.7 | 1 | CH$_3$ (11) |
| 21.7 | 1 | CH$_2$ (10) |
| 23.7 | 1 | CH$_3$ (13) |
| 26.7 | 1 | CH$_2$ (9) |
| 31.5 | 1 | CH$_2$ (8) |
| 76.4 | 1 | CH(7) |
| 114.9-117.3-126.9 | 3 | CH aromatic (3, 5, 6) |
| 124.6 | 1 | Quaternary C aromatic (2) |
| 133.2 | 1 | Quaternary C aromatic (4) |
| 156.0 | 1 | Quaternary C aromatic (1) |
| 168.1-172.0 | 2 | C=O (12, 14) |
| 189.0 | 1 | CH (aldehyde) |

D. 2-n-Butyl-5-N-acetamidobenzofuran (Compound VIII: R$_1$=n-C$_4$H$_9$; R$_3$=CH$_3$)

1 g of benzenesulfonyl chloride and 1 ml of toluene are placed in a round-bottomed flask. The mixture is stirred, 1.3 g of triethylamine (3.6 equivalents) are introduced and stirring is continued at 80° C. for 20 minutes, during which time the reaction medium becomes increasingly dark. A solution of 1 g of 2-(2-formyl-4-N-acetamidophenoxy)hexanoic acid (compound VII) (0.00355 mol; 1 equivalent) in 3 ml of toluene and 2 ml of methyl tert-butyl ether is then introduced. The mixture is heated at 80° C. for 2 hours while monitoring the reaction kinetics by gas chromatography. The reaction mixture is cooled to about 50° C. and hydrolyzed by adding 4 ml of water. The toluene phase and the aqueous phase are separated by settling. 2 ml of water and 0.2 ml of 36% hydrochloric acid are added to this organic phase. The mixture is stirred for 5 minutes and the two phases are then separated by settling. The toluene phase is washed with 2 ml of water, and the two phases are separated by settling. The organic phase is washed with a solution of 0.9 g of sodium hydroxide at 23% in 1.5 ml of water. The mixture is stirred, the toluene phase is separated out by settling and washed with 2 g of 10% sodium chloride solution. The two phases are separated by settling and the toluene phase is concentrated on a rotary evaporator to recover 1.1 g of desired compound in the form of a brown oil.

$^1$H NMR (CDCl$_3$)

| Chemical shifts δ ± 0.01 ppm | Multiplicity | Integration | Coupling constants (|J| ± 0.5 Hz) | Assignment |
|---|---|---|---|---|
| 0.94 | Triplet | 3 | $^3J_{CH3-CH2}$ = 7.5 Hz | CH$_3$ (12) |
| 1.40 | Sextet | 2 | $^3J_{CH2-CH3}$ =<br>$^3J_{CH2-CH2}$ = 7.5 Hz | CH$_2$ (11) |
| 1.70 | Quintet | 2 | $^3J_{CH2-CH2}$ = 7.5 Hz | CH$_2$ (10) |
| 2.14 | Singlet | 3 | — | CH$_3$ (13) |
| 2.73 | Triplet | 2 | $^3J_{CH2-CH2}$ = 7.5 Hz | CH$_2$ (9) |
| 6.29 | Singlet | 1 | — | H (2) |
| 7.12 | Doubled doublet | 1 | $^3J_{H5-H6}$ = 8.5 Hz<br>$^4J_{H5-H3}$ = 2.0 Hz | H (5) |
| 7.28 | Doublet | 1 | $^3J_{H6-H5}$ = 8.5 Hz | H (6) |
| 7.64 | Broad singlet | 1 | — | NH |
| 7.72 | Doublet | 1 | $^4J_{H3-H5}$ = 2.0 Hz | H (3) |

$^{13}$C NMR (CDCl$_3$)

| Chemical shifts δ ± 0.1 ppm | Number of carbons | Assignment |
|---|---|---|
| 13.8 | 1 | CH$_3$(12) |
| 22.3 | 1 | CH$_2$(11) |
| 24.4 | 1 | CH$_3$(13) |
| 28.2 | 1 | CH$_2$(10) |
| 29.8 | 1 | CH$_2$(9) |
| 102.1 | 1 | CH(2) |
| 110.6-112.5-116.5 | 3 | CH(3), CH(5), CH(6) |
| 129.5-132.8-151.8-160.8-168.6 | 5 | Aromatic quaternary carbons (1, 4, 7, 8) and C=O(14) |

E. 2-n-Butyl-3-(4-methoxybenzoyl)-5-N-acetamido-benzofuran (Compound X: $R_1$=n-$C_4H_9$; $R_3$=$CH_3$; $R_5$=$CH_3$)

10 g of 2-n-butyl-5-N-acetamidobenzofuran (compound VIII) (0.04 mol; 1 equivalent) and then a solution of 29.4 g of 4-methoxybenzoyl chloride (compound IX) (0.054 mol; 1.25 g equivalents) in dichloroethane are placed in a 250 ml reactor. The whole is stirred at 40° C. until dissolution is complete, and 8.8 g of ferric chloride (0.054 mol; 1.25 equivalents) are then added portionwise. The temperature is maintained at 40° C. for 1 hour while monitoring the reaction progress. The reaction medium is hydrolyzed by adding 100 ml of water, and is heated to 50° C. The two phases are then separated by settling, and the organic phase is recovered and concentrated under vacuum on a rotary evaporator. 21 g of an orange oil which forms crystals are thus obtained. This oil is taken up in 40 ml of ethyl acetate (2 volumes) and brought to reflux in a round-bottomed flask, which brings about dissolution of the crystals. The reaction medium is allowed to cool to room temperature with stirring, which brings about the appearance of a precipitate, which is kept in contact with an ice bath (5° C.) for 10 minutes. The reaction medium is filtered and pale yellow crystals are recovered. These crystals are dried in a vacuum oven at 50° C. to give 10.1 g of crystals. These crystals are taken up in ethyl acetate (4 volumes) and the whole is then refluxed until dissolution is complete. The reaction medium is allowed to cool to room temperature, and the crystals formed are then filtered off through a sinter. The crystals obtained are rinsed with 10 ml of ethyl acetate and dried in an oven at 50° C. to give 8.2 g of desired compound in the form of a first crop of crystals (organic purity: 99.7%) and 1.3 g of the same compound in the form of a second crop of crystals (organic purity: 99.1%).

$^1$H NMR (CDCl$_3$)

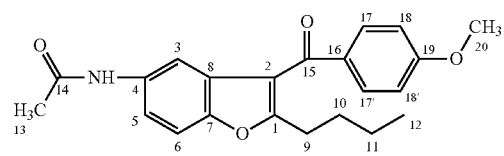 [SMILES: CCCCc1oc2ccc(NC(C)=O)cc2c1C(=O)c1ccc(OC)cc1]

| Chemical shifts δ ± 0.01 ppm | Multiplicity | Integration | Coupling constants (\|J\| ± 0.5 Hz) | Assignment |
|---|---|---|---|---|
| 0.86 | Triplet | 3 | $^3J_{CH3-CH2}$ = 7.5 Hz | CH$_3$ (12) |
| 1.32 | Sextet | 2 | $^3J_{CH2-CH3}$ = $^3J_{CH2-CH2}$ = 7.5 Hz | CH$_2$ (11) |
| 1.71 | Quintet | 2 | $^3J_{CH2-CH2}$ = 7.5 Hz | CH$_2$ (10) |
| 2.08 | Singlet | 3 | — | CH$_3$ (13) |
| 2.84 | Triplet | 2 | $^3J_{CH2-CH2}$ = 7.5 Hz | CH$_2$ (9) |
| 3.86 | Singlet | 3 | — | CH$_3$ (20) |
| 6.93 | Doublet (AB system) | 2 | $^3J_{H18-H17}$ = 9.0 Hz $^3J_{H18'-H17'}$ = 9.0 Hz | H (18, 18') |
| 7.32 | Doublet | 1 | $^4J_{H3-H5}$ = 2.0 Hz | H (3) |
| 7.36 | Doublet | 1 | $^3J_{H6-H5}$ = 9.0 Hz | H (6) |
| 7.54 | Doubled doublet | 1 | $^3J_{H5-H6}$ = 9.0 Hz $^4J_{H5-H3}$ = 2.0 Hz | H (5) |
| 7.57 | Broad singlet | 1 | — | NH |
| 7.80 | Doublet (AB system) | 2 | $^3J_{H17-H18}$ = 9.0 Hz $^3J_{H17'-H18'}$ = 9.0 Hz | H (17, 17') |

$^{13}$C NMR (CDCl$_3$)

| Chemical shifts δ ± 0.1 ppm | Number of carbons | Assignment |
|---|---|---|
| 13.7 | 1 | CH$_3$ (12) |
| 22.4 | 1 | CH$_2$ (11) |
| 24.3 | 1 | CH$_3$ (13) |
| 28.0 | 1 | CH$_2$ (10) |
| 30.1 | 1 | CH$_2$ (9) |
| 55.5 | 1 | CH$_3$ (20) |
| 111.0-113.0-118.2 | 3 | CH(3), CH(5), CH(6) |
| 113.8 | 2 | CH (18, 18') |
| 131.7 | 2 | CH (17, 17') |
| 116.9-127.5-131.7-133.8-150.7-163.6-165.4-168.5 | 8 | Aromatic quaternary carbons (1, 2, 4, 7, 8, 16, 19) and C=O(14) |
| 190.4 | 1 | C=O(15) |

F. 2-n-Butyl-3-(4-hydroxybenzoyl)-5-N-acetamido-benzofuran (Compound XI: $R_1$=n-$C_4H_9$; $R_3$=$CH_3$)

5 g of 2-n-butyl-3-(4-methoxybenzoyl)-5-N-acetamido-benzofuran (compound X) (0.0137 mol; 1 equivalent) and 15 ml of chlorobenzene (3 volumes) are placed in a 250 ml reactor. The mixture is stirred at 60° C. until the methoxy derivative is partially dissolved, followed by addition, in a single portion, of 5.5 g of aluminum chloride (0.0411 mol; 3 equivalents), which brings about a change in the reaction medium. The methoxy derivative is dissolved and a temperature of 60° C. is maintained for 4 hours. The mixture is then hydrolyzed by adding 15 ml of water (3 volumes) while stirring at about 45° C.±5° C. The reaction medium is then extracted with n-butanol at a temperature of about 45° C. The two phases are separated by settling while hot. A butanol phase is thus recovered, in which is observed a precipitate which appears when the temperature lowers. The organic phase is filtered and 2 g of a white product are thus recovered. The filtrate is concentrated under vacuum on a rotary evaporator and the 4 g of oil thus obtained and the precipitate are then taken up in ethyl acetate (2 volumes). The medium is then heated to reflux to dissolve the particles, and is allowed to cool to room temperature. The crystals obtained are filtered off and 1.3 g of a slightly yellow product are thus recovered (organic purity: 97.9%). A further recrystallization from ethyl acetate is performed using the filtrate obtained, which makes it possible to recover 0.8 g of desired compound with an organic purity of 96.6%.

$^1$H NMR (DMSO-d$_6$)

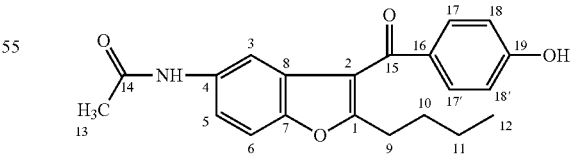

| Chemical shifts δ ± 0.01 ppm | Multiplicity | Integration | Coupling constants (\|J\| ± 0.5 Hz) | Assignment |
|---|---|---|---|---|
| 0.77 | Triplet | 3 | $^3J_{CH3-CH2}$ = 7.5 Hz | CH$_3$ (12) |
| 1.21 | Sextet | 2 | $^3J_{CH2-CH3}$ = $^3J_{CH2-CH2}$ = 7.5 Hz | CH$_2$ (11) |
| 1.61 | Quintet | 2 | $^3J_{CH2-CH2}$ = 7.5 Hz | CH$_2$ (10) |

-continued

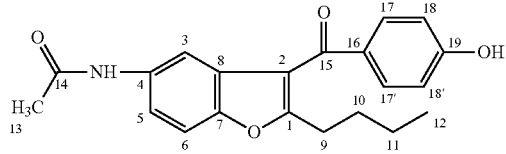

| Chemical shifts δ ± 0.01 ppm | Multiplicity | Integration | Coupling constants (\|J\| ± 0.5 Hz) | Assignment |
|---|---|---|---|---|
| 1.98 | Singlet | 3 | — | $CH_3$ (13) |
| 2.75 | Triplet | 2 | $^3J_{CH2-CH2}$ = 7.5 Hz | $CH_2$ (9) |
| 6.87 | Doublet | 2 | $^3J_{H18-H17}$ = 8.5 Hz $^3J_{H18'-H17'}$ = 8.5 Hz | H (18, 18') |
| 7.51 | Multiplet | 2 | — | H (3), H (5), |
| 7.64 | Doublet | 1 | | H (6) |
| 7.66 | Doublet | 2 | $^3J_{H17-H18}$ = 8.5 Hz $^3J_{H17'-H18'}$ = 8.5 Hz | H (17, 17') |
| 9.90 | Broad singlet | 1 | — | NH or OH |
| 10.43 | Very broad singlet | 1 | | NH or OH |

$^{13}C$ NMR (DMSO-$d_6$)

| Chemical shifts δ ± 0.1 ppm | Number of carbons | Assignment |
|---|---|---|
| 13.3 | 1 | $CH_3$ (12) |
| 21.5 | 1 | $CH_2$ (11) |
| 23.8 | 1 | $CH_3$ (13) |
| 27.0 | 1 | $CH_2$ (10) |
| 29.4 | 1 | $CH_2$ (9) |
| 110.7-116.5 | 3 | CH(3), CH(5), CH(6) |
| 115.3 | 2 | CH (18, 18') |
| 131.5 | 2 | CH (17, 17') |
| 116.5-126.7-129.4-135.4- | 8 | Aromatic quaternary |
| 149.1-162.2-163.4-167.9 | | carbons (1, 2, 4, 7, 8, 16, 19) and C=O(14) |
| 189.1 | 1 | C=O(15) |

G. 2-n-Butyl-3-{4-[3-(di-n-butylamino)propoxy]benzoyl}-5-N-acetamidobenzofuran (Compound II: $R_1$=n-$C_4H_9$; $R_2$=3-(di-n-butylamino)propyl; $R_3$=$CH_3$)

4 g of 2-n-butyl-3-(4-hydroxybenzoyl)-5-N-acetamidobenzofuran (compound XI) (0.0114 mol; 1 equivalent), 2.1 g of potassium carbonate (1.3 equivalents) and 15 ml of methyl ethyl ketone are placed in a three-necked round-bottomed flask. The reaction medium is stirred, and 2.8 g of 1-chloro-3-(di-n-butylamino)propane (compound XII) (0.0137 mol; 1.2 equivalents) are added at a temperature of 80° C. and the whole is heated at the reflux temperature of the methyl ethyl ketone for at least 8 hours. The white deposit formed around the flask is recovered and is then stirred again by adding a further 0.1 equivalent of chloramine. Heating is continued for about 5 hours and the reaction medium is then concentrated under vacuum on a rotary evaporator. The oil thus obtained is taken up in 15 ml of water and 15 ml of methyl tert-butyl ether, and the two phases are separated by settling. The organic phase is washed with 0.5 equivalent of acetic acid in 15 ml of water. The mixture is stirred, the phases are separated by settling and the organic phase is washed with 15 ml of water. This organic phase is concentrated, and 5.2 g of desired compound are thus recovered in the form of a whitish oil.

$^1H$ NMR ($CDCl_3$)

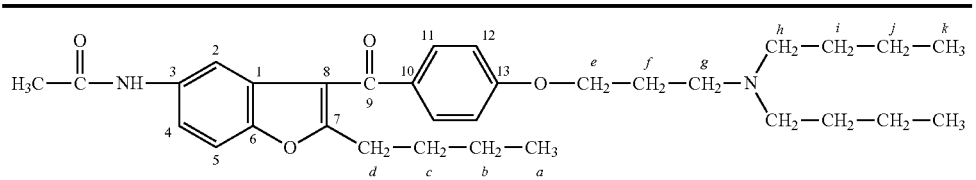

| Chemical shifts δ ± 0.01 ppm | Multiplicity | Integration | Assignment |
|---|---|---|---|
| 0.87 | Triplet | 3 | $CH_3$ (a) |
| 0.89 | Triplet | 6 | 2× $CH_3$ (k) |
| 1.31 | Sextet | 6 | $CH_2$ (b) 2× $CH_2$ (j) |
| 1.48 | Multiplet | 4 | 2× $CH_2$ (i) |
| 1.72 | Quintet | 2 | $CH_2$ (c) |
| 2.00 | Multiplet | 2 | $CH_2$ (f) |
| 2.09 | Singlet | 3 | $CH_3$—C=O |
| 2.54 | Triplet | 4 | 2× $CH_2$ (h) |
| 2.72 | Triplet | 2 | $CH_2$ (g) |
| 2.85 | Triplet | 2 | $CH_2$ (d) |
| 4.07 | Triplet | 2 | $CH_2$ (e) |
| 6.91 | Doublet | 2 | 2× CH (12) |
| 7.26 | Doublet | 1 | CH (2) |
| 7.37 | Doublet | 1 | CH (5) |
| 7.61 | Doubled doublet | 1 | CH (4) |

EXAMPLE 2-n-Butyl-3-{4-[3-(di-n-butylamino)propoxy]benzoyl}-5-aminobenzofuran hydrochloride (Compound I: $R_1$=n-$C_4H_9$; $R_2$=3-(di-n-butylamino)propyl)

1 equivalent of 2-n-butyl-3-{4-[3-(di-n-butylamino)propoxy]benzoyl}-5-N-acetamidobenzofuran (compound II) and 4 volumes of ethanol are placed in a reactor. 6 equivalents of 36% hydrochloric acid are then added and the reaction medium is heated to reflux, which brings about formation of the desired hydrochloride. The reaction medium is then washed, at room temperature, with aqueous sodium carbonate solution so as to liberate this hydrochloride, which passes into the aqueous phase, from which it is extracted.

In this manner, the desired compound is obtained in an organic purity of 93%.

Degree of conversion of compound II: 100%

The conversion of 2-n-butyl-3-{4-[3-(di-n-butylamino)propoxy]benzoyl}-5-aminobenzofuran hydrochloride into dronedarone hydrochloride is then performed as described in patent EP 0 471 609.

What is claimed is:

1. An N-phenylalkylamide derivative of formula XIII:

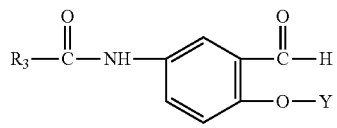

XIII wherein $R_3$ represents a linear or branched $C_1$-$C_4$ alkyl group and Y represents a group of formula XIV:

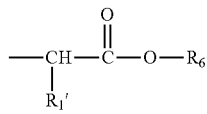

XIV wherein $R_1'$ and $R_6$ each independently represent hydrogen or a linear or branched $C_1$-$C_4$ alkyl group.

2. The N-phenylalkylamide derivative according to claim 1, wherein $R_3$ represents methyl and Y represents the group XIV in which $R_1'$ represents n-butyl and $R_6$ represents methyl.

3. The N-phenylalkylamide derivative according to claim 1, wherein $R_3$ represents methyl and Y represents the group XIV wherein $R_1'$ represents n-butyl and $R_6$ represents hydrogen.

* * * * *